United States Patent
Wejdemann et al.

(10) Patent No.: US 10,139,357 B2
(45) Date of Patent: Nov. 27, 2018

(54) X-RAY MULTIGRAIN CRYSTALLOGRAPHY

(71) Applicant: Xnovo Technology ApS, Koge (DK)

(72) Inventors: Christian Wejdemann, Roskilde (DK);
Henning Friis Poulsen, Roskilde (DK);
Erik Mejdal Lauridsen, Harlev (DK);
Peter Reischig, Leicester (GB)

(73) Assignee: Xnovo Technology ApS, Koge (DK)

( * ) Notice: Subject to any disclaimer, the term of this patent is extended or adjusted under 35 U.S.C. 154(b) by 169 days.

(21) Appl. No.: 15/228,868

(22) Filed: Aug. 4, 2016

(65) Prior Publication Data
US 2017/0038317 A1  Feb. 9, 2017

(30) Foreign Application Priority Data
Aug. 7, 2015   (EP) ...................................... 15180196

(51) Int. Cl.
*G01N 23/207*   (2018.01)
*G01N 23/2055*  (2018.01)

(52) U.S. Cl.
CPC ....... *G01N 23/207* (2013.01); *G01N 23/2055* (2013.01); *G01N 2223/606* (2013.01)

(58) Field of Classification Search
CPC ............. G01N 23/2055; G01N 23/207; G01N 2223/606
USPC ......................................................... 378/73
See application file for complete search history.

(56) References Cited

U.S. PATENT DOCUMENTS

| | | | |
|---|---|---|---|
| 8,131,481 B2 * | 3/2012 | Moeck | G01N 23/20058 702/27 |
| 9,222,900 B2 * | 12/2015 | Lauridsen | G01N 23/207 |
| 2003/0198997 A1 * | 10/2003 | Von Dreele | G01N 23/207 435/7.1 |
| 2014/0307854 A1 | 10/2014 | Lauridsen et al. | |

OTHER PUBLICATIONS

"X-ray diffraction contrast tomography: a novel technique for three dimensional grain mapping of polycrystals" Journal of Applied Chrystallography (2008) to Ludwig et al.*
Extended European Search Report dated Jan. 29, 2016 for European application No. 15180196.6-1559.
(Continued)

*Primary Examiner* — Kenneth J Malkowski
(74) *Attorney, Agent, or Firm* — Fox Rothschild LLP; Carol E. Thorstad-Forsyth (57) ABSTRACT

Disclosed is method of determining one or more unit cells of a polycrystalline sample and indexing a set DV of 3D diffraction vectors. The method comprising obtaining a plurality of candidate first lattice plane normal vectors and a plurality of candidate second lattice plane normal vectors for a particular unknown grain; using said plurality of candidate first lattice plane normal vectors and said plurality of candidate second lattice plane normal vectors to select a plurality of subsets SSDV_n of the set DV of 3D diffraction vectors and processing said plurality of subsets SSDV_n of 3D diffraction vectors to determine a primary candidate unit cell PCUC defined by three lattice vectors; wherein the primary candidate unit cell PCUC is validated by evaluating the fit of the PCUC with the full set DV of 3D diffraction vectors.

14 Claims, 4 Drawing Sheets

(56) References Cited

OTHER PUBLICATIONS

Sorensen, H.O., et al., Multigrain Crystallography,: Zeitschrift Fuer Kristallographie, vol. 227, No. 1, Jan. 1, 2012, pp. 63-78, XP055242806, DE, ISSN: 0044-2968, DOI: 10.1524/zkri.2012.1438.

Schmidt, Soren, "GrainSpotter: A Fast and Robust Polycrystalline Indexing Algorithm," Journal of Applied Crystallography, vol. 47, No. 1, Feb. 1, 2014, pp. 276-284, XP055242808, DOI: 10/1107/S160057671303185.

Wejdemann, C., et al., "Multigrain Indexing of Unknown Multiphase Materials," Journal of Applied Crystallography, ISSN 1600-5767, J. Appl. Cryst. 2016, 49, 616-621.

King, A., et al., "First Laboratory X-Ray Diffraction Contrast Tomography for Grain Mapping of Polycrystals," Journal of Applied Crystallography, ISSN 0021-8898, J. Appl. Cryst. 2013, 46, 1734-1740.

Larson, B.C., et al., "Three-Dimensional X-Ray Structural Microscopy with Submicrometre Resolution," Letters to Nature, copyright 2002 Macmillan Magazines Ltd., vol. 415, Feb. 21, 2002.

Ludwig, W., et al., "Three-Dimensional Grain Mapping by X-Ray Diffraction Contrast Tomography and the Use of Friedel Pairs in Diffraction Data Analysis," Review of Scientific Instruments, 80, 033905, copyright 2009 American Institute of Physics, 0034-6748/2009/80(3)/033905/9.

Lauridsen, E.M., et al., "Tracking: A Method for Structural Characterization of Grains in Powders or Polycrystals," Journal of Applied Crystallography, ISSN 0021-8898, J. Appl. Cryst. (2001), 34, 744-750.

Ungar, T., et al., "Burgers Vector Population, Dislocation Types and Dislocation Densities in Single Grains Extracted from a Polycrystalline Commercial-Purity Ti Specimen by X-Ray Line-Profile Analysis," ScienceDirect, Scripta Materialia 63 (2010) 69-72, DOI 10.1016/j.scriptamat.2010.03.016.

Schmidt, S., "GrainSpotter: A Fast and Robust Polycrystalline Indexing Algorithm," Journal of Applied Crystallography, ISSN 1600-5767, J. Appl. Cryst. (2014) 47, 276-284, doi: 10.1107/S1600576713030185.

Wejdemann, C., et al., "In Situ Observation of the Dislocation Structure Evolution During a Strain Path Change in Copper," JOM, vol. 65, No. 1, 2013, doi: 10.1007/s11837-012-0504-0, copyright 2012 The Authors.

Jakobsen, B., et al., "Direct Determination of Elastic Strains and Dislocation Densities in Individual Subgrains in Deformation Structures," Science Direct, Acta Materialia 55 (2007) 3421-3430, 1359-6454, copyright 2007 Acta Materilia Inc., doi: 10.1016/j.actamat.2007.01.049.

Gruber, B., "The Relationship between Reduced Cells in a General Bravais Lattice," Acta Aryst. (1973). A29, 433.

Grosse-Kunstleve, R.W., et al., "Numerically Stable Algorithms for the Computation of Reduced Unit Cells," Acta Crystallographica Section A, Foundations of Crystallography ISSN 0108-7673, copyright 2004, A60, 1-6, DOI: 10.1107/S010876730302186X.

\* cited by examiner

*Fig. 10b*

X-RAY MULTIGRAIN CRYSTALLOGRAPHY

RELATED APPLICATION DATA

The present application claims benefit of European Patent Application No. EP15180196, filed on Aug. 7, 2015 and entitled "X-RAY MULTIGRAIN CRYSTALLOGRAPHY", the contents of which are incorporated herein by reference in its entirety.

FIELD

The present invention relates to X-ray multigrain crystallography, particular to a method of determining one or more unit cells of a poly-crystalline sample and indexing 3D diffraction vectors, to a method of indexing diffraction spots, to a method of determining the composition of a poly-crystalline material, and to an X-ray diffraction apparatus.

BACKGROUND

X-ray crystallography is an important tool for analysing crystals and has a central role in technical fields such as mineralogy, metallurgy, biology, and pharmacology. Traditionally X-ray crystallography has been based on either single crystals or powders. Single crystal X-ray crystallography provide superior information compared to powder X-ray crystallography but require larger crystals. Thus, a significant amount of work has to be performed in e.g. pharmacology for growing mono grain crystallites of a size and quality required for X-ray crystallography analysis.

X-ray multigrain crystallography is a relatively new approach [1] and complementary to traditional crystallographic analysis which is based on either single crystals or powders. The experimental set-up is in the simplest case identical to that typically used in single crystal X-ray crystallography, with a monochromatic beam, a fully illuminated sample in transmission geometry on a rotary table and a 2D detector. The images acquired during a rotation of the sample may comprise up to a million diffraction spots from the grains simultaneously illuminated. A key step in the analysis of such data is multigrain indexing, i.e. associating diffraction spots with their crystal of origin.

Traditionally multigrain indexing requires a priori knowledge of the sample material and structure. At least the space group and the unit cells of the grains need to be known a priori in prior art indexing methods. The unit cell corresponds to the physical crystal lattice of a particular unknown grain and is defined by three lattice vectors. Hence, a brute force search and optimization procedure in the 9D space, spanned by these three lattice vectors, will provide an indexing of all grains. However, to our knowledge, such an approach is computationally not feasible.

Thus, it remains a problem to provide a more computational efficient method for indexing grains.

SUMMARY OF THE INVENTION

According to a first aspect the present invention relates to a method of determining one or more unit cells of a poly-crystalline sample and indexing a set DV of 3D diffraction vectors obtained by illuminating said poly-crystalline sample with an X-ray source at one or more orientations and recording diffraction spots using a at least one 2D or 3D X-ray detector for each of said one or more orientations, said set DV of 3D diffraction vectors being indexed into one or more grains, said method comprising the steps of:

(A) obtaining a plurality of candidate first lattice plane normal vectors and a plurality of candidate second lattice plane normal vectors for a particular unknown grain; using said plurality of candidate first lattice plane normal vectors and said plurality of candidate second lattice plane normal vectors to select a plurality of subsets SSDV_n of the set DV of 3D diffraction vectors and processing said plurality of subsets SSDV_n of 3D diffraction vectors to determine a primary candidate unit cell PCUC defined by three lattice vectors; wherein the correspondence of the primary candidate unit cell PCUC is validated by evaluating the fit of the PCUC with the full set DV of 3D diffraction vectors; and (B) determining if the fit of primary candidate unit cell PCUC with the full set DV of 3D diffraction vectors is above a first threshold;

wherein if the fit of the primary candidate unit cell PCUC is above said first threshold the primary candidate unit cell PCUC is used to identify a subset ST of the set DV of 3D diffraction vectors originating from a single grain in the poly-crystalline sample, said subset ST is indexed wherein the method returns to step (A) unless a predetermined criteria has been reached.

Consequently, by using candidate lattice plane normal vectors to reduce the full set DV of 3D diffraction vectors and using said reduced set to find a primary candidate unit cell PCUC a more computational efficient method of indexing diffraction vectors is provided.

Furthermore, by validating the primary candidate unit cell PCUC on the full set DV of diffraction vectors the indexing may be done with high accuracy.

The X-ray source may preferably be a monochromatic source and the at least one X-ray detector may preferably be a 2D detector. However, the X-ray source may also be a polychromatic source, and the at least one X-ray detector may be a 3D detector capable of separating different X-ray energies.

Figure 10A:
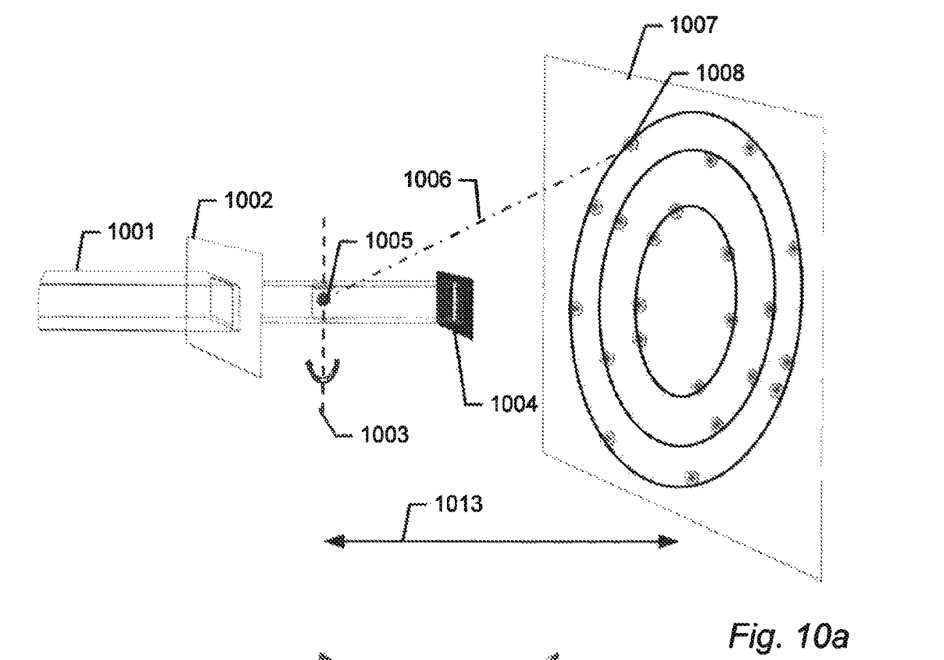
FIGS. 10a-b show schematically how diffraction spots may be recorded and transformed into diffraction vectors.
Figure 10B:
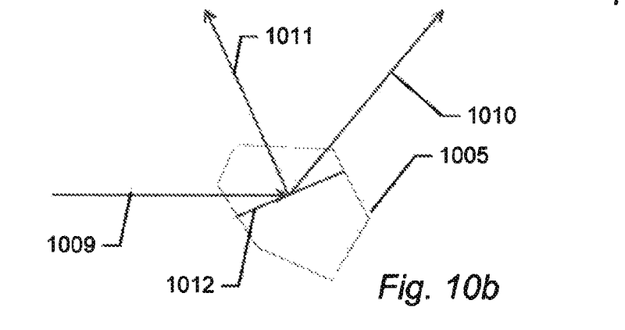

The measurement setup may be similar to the measurement setup used in single crystal X-ray crystallography, see FIGS. 10ab for details of how diffraction spots may be recorded and transformed into diffraction vectors. The candidate first and second lattice plane normal vectors may be generated using a pseudo random number generator (PRNG). Alternatively they may be selected from a pre-generated list.

The polycrystalline sample may be any material sample that contains at least one crystal or a multiple of crystals, it may contain multiple phases, may be in a solid or powder form, may be a mixture, may contain non-crystalline material, such as a matrix or a liquid.

The predetermined criteria may be that the method determines that all indexable grains in the poly-crystalline sample have been indexed, that a predetermined number of grains have been indexed, that a predetermined percentage of the diffraction vectors has been indexed, that the remaining diffraction vectors is below a predetermined number, or that step (A) and (B) have been repeated a predetermined number of times without identifying any new grains.

The method of the present invention provides indexed candidate grains, and further analysis and processing may be performed to improve or provide a reconstructed model of the sample. The known tools used in single crystal crystallography may be applied for such further analysis and processing.

The primary candidate unit cell may be either smaller or larger than the real unit cell of the grain or it may be given by a non-standard set of lattice vectors. Thus the primary candidate unit may be further optimized before it is used to index diffraction vectors e.g. by determining a standard reduced unit cell e.g. using methods disclosed in [2] or [3].

In some embodiments, the subset ST is removed from the set DV of 3D diffraction vectors before the method returns step (A).

In some embodiments, step (A) comprises the steps of:
(a) selecting a set L1 of candidate first lattice plane normal vectors;
(b) evaluating the fit of each candidate first lattice plane normal vector of the set L1 with the set DV of 3D diffraction vectors;
(c) selecting a subset SL1 of the set L1 comprising the N1 candidate first lattice plane normal vectors having the best fit with the set DV of 3D diffraction vectors;
(d) performing steps (d_a) to (d_g) for each candidate first lattice plane normal vector n of the subset SL1:
(d_a) using said candidate first lattice plane normal vector n to select a subset SDV_n of the set DV of 3D diffraction vectors;
(d_b) selecting a set L2_n of candidate second lattice plane normal vectors;
(d_c) evaluating the fit of each candidate second lattice plane normal vector of the set L2_n with the subset SDV_n of 3D diffraction vectors;
(d_d) selecting a subset SL2_n of the set L2_n comprising the N2 candidate second lattice plane normal vectors having the best fit with the subset SDV_n of 3D diffraction vectors;
(d_e) using said subset SL2_n of candidate second lattice plane normal vectors to select a subset SSDV_n of the subset SDV_n of 3D diffraction vectors;
(d_f) processing said subset SSDV_n of 3D diffraction vectors to determine a candidate unit cell CUC_n defined by three lattice vectors;
(d_g) evaluating the fit of the candidate unit cell CUC_n with the set DV of 3D diffraction vectors;
wherein the candidate unit cell of the N1 candidate unit cells CUC_n (n=1 to N1) having the best fit with the full set DV of 3D diffraction vectors is selected as the primary candidate unit cell PCUC.

Consequently, by evaluating the fit of a plurality of candidate first lattice plane normal vectors with the set DV of 3D diffraction vectors, no a priori knowledge is needed to identify true candidates as a base line for untrue candidate first lattice plane normal vectors may automatically be generated. Similar, by finding a plurality of candidate unit cells a base line for untrue candidate unit cells may be generated. Furthermore, by reducing the set DV of diffraction vectors before the search for a true second lattice plane normal vector is initiated (resulting in the subset SDV_n), and again before the candidate unit cell CUC_n is found (resulting in the set SSDV_n), the speed of the method is further improved.

The set L1 may comprise at least 20, 100, 1000 or 10000 candidate first lattice plane normal vectors. The set L2_n may comprise at least 20, 100, 1000, or 10000 candidate second lattice plane normal vectors. The sets L1 and L2_n may be generated using a PRNG. Alternatively the sets may be selected from a pre-generated list. N1 may be at least 2, 5 or 10.

In some embodiments, step (b) comprises the steps of:
(b1) performing steps (b1_a) and (b1_b) for each j candidate first lattice plane normal vector of the set L1:
(b1_a) projecting the set DV of 3D diffraction vectors onto said j candidate first lattice plane normal vector resulting in a set DV1D_j of projected 1D diffraction vectors;
(b1_b) filtering the set DV1D_j of projected 1D diffraction vectors with a plurality of filters comprising a regular array of box functions, the width of the boxes being the same for all filters but the distance 'd' between the boxes is increased from a value d_min to a value d_max (preferably in increasingly larger steps), the output of each filtering process K is the normalised number of projected 1D diffraction vectors that are positioned within a box function, wherein the highest K value is used as a measure of the fit of the n'th candidate first lattice plane normal vector with the set DV of 3D diffraction vectors; and wherein step (c) comprises selecting the N1 candidate first lattice plane normal vectors having the highest K value.

Consequently, an efficient method of identifying potential true candidate 5 first lattice plane normal vectors is provided. By reducing the 3D data set DV to a 1D dataset DV1D_j before the filtering process, the complexity is reduced.

The d_min value may be a value>q_min and the d_max value may be given by q_max/2, where q_min is the length of the smallest possible diffraction vector and q_max is the length of largest possible diffraction vector q_min may be selected to be the smallest possible value for any material or if knowledge of the type of material of the sample is available, that knowledge may be used to select q_min. Correspondingly, q_max may be selected to be the largest possible value for any material or if knowledge of the type of material of the sample is available, that knowledge may be used to select q_max.

The width of the boxes may be selected to be 2e where e is the experimentally established center-of-mass errors of the position of the reflections in reciprocal space The output K is normalized to take account of the diffraction vectors that by chance are positioned within a box. This may be done by subtracting from the count a number given by equation 1 below:

$$\frac{w}{d} \cdot N\_DV \qquad (1)$$

where w is the width of the boxes, d is the distance between the centre of each box, and N_DV is the number of diffraction vectors in the set DV. Thus, highest K value should be close to zero for an untrue candidate first lattice plane normal vector.

In some embodiments, step (c) further comprises for each n candidate first lattice plane normal vector of the subset SL1, optimizing the n candidate first lattice plane normal vector by performing a local grid search resulting in an subset SL1* of optimized candidate first lattice plane normal vectors, wherein the optimized subset SL1* is used in step (d).

In some embodiments, step (d_a) comprises selecting the 3D diffraction vectors of the set DV that when they are projected onto said n candidate first lattice plane normal vector are positioned within a box function for the filter having the highest K value.

For true candidate first lattice plane normal vectors this result in a subset that contains all or almost all of the diffraction vectors from one particular grain but also a significant number of reflections for other grains that by chance happen to be projected such that they fall within the boxes.

In some embodiments, the step (d_c) comprises the steps of:
- (d_c1) performing steps (d_c1_a) and (d_c1_b) for each k candidate second lattice plane normal vector of the set L2_n:
- (d_c1_a) projecting the subset SDV_n of 3D diffraction vectors onto said k candidate second lattice plane normal vector resulting in a set SDV_n1D_n of projected 1D diffraction vectors;
- (d_c1_b) filtering the set SDV_n1D_k of projected 1D diffraction vectors with a plurality of filters comprising a regular array of box functions, the width of the boxes being the same for all filter but the distance 'd' between the boxes is increased from a value d_min to a value d_max (preferably in increasingly larger steps), the output of each filtering process K is the normalized number of projected 1D diffraction vectors that are positioned within a box function, wherein the highest K value is used as a measure of the fit of the k'th candidate second lattice plane normal vector with the set SDV_n of 3D diffraction vectors; and wherein step (d_d) comprises selecting the N3 candidate second lattice plane normal vectors having the highest K value.

In some embodiments, step (d_d) further comprises for each k candidate second lattice plane normal vector of the subset SL2_n, optimizing the k candidate second lattice plane normal vector by performing a local grid search resulting in an subset SL2_n* of optimized candidate second lattice plane normal vectors, wherein the optimized subset SL2_n* is used in step (d_e).

Consequently, candidate second lattice plane normal vectors may more precisely correspond to true lattice plane normal vectors. This may improve the speed of the method and improve the precision of the indexing.

In some embodiments, the candidate second lattice plane normal vector CL2_n of the subset SL2_n* having the best fit with the subset SDV_n of 3D diffraction vectors is used to select the subset SSDV_n of the subset SDV_n of 3D diffraction vectors.

In some embodiments, step (d_e) comprises selecting the 3D diffraction vectors of the subset SDV_n that when they are projected onto CL2_n are positioned within a box function for the filter having the highest K value.

In some embodiments, step (d_f) comprises the steps of:
- (d_f_a) selecting a subset SSSDV_n of the subset SSDV_n of 3D diffraction vectors;
- (d_f_b) determining the normal vector for all planes spanned by three diffraction vectors of the subset SSSDV_n of 3D diffraction vectors (ignoring sets of three diffraction vectors having a cross product close to zero) each normal vector being a candidate lattice plane normal vector thereby resulting in a set NL_n of new candidate lattice plane normal vectors;
- (d_f_c) evaluating the fit of each new candidate lattice plane normal vector of the set NL_n with the subset SSDV_n of 3D diffraction vectors; and
- (d_f_d) determining a candidate unit cell CUC_n.

Consequently, by finding new candidate lattice plane normal vectors the risk of choosing an ambiguous candidate unit cell is lowered.

The subset SSSDV_n may be the X shortest diffraction vectors of the subset SSDV_n. X may be any number between 5 and 500, 10, and 250, or 20 and 100 e.g. the 50 shortest diffraction vectors.

In some embodiments, step (d_f_c) comprises:
- (d_f_c1) performing steps (d_f_c1_a) and (d_f_c1_b) for each i new candidate lattice plane normal vector of the set NL_n:
- (d_f_c1_a) projecting the subset SSDV_n of 3D diffraction vectors onto said i new candidate lattice plane normal vector resulting in a set SSDV_n_1D_i of 1D diffraction vectors;
- (d_f_c1_b) filtering the set SSDV_n_1D_i of projected 1D diffraction vectors with a plurality of filters comprising a regular array of box functions, the width of the boxes being the same for all filter but the distance 'd' between the boxes is increased between a value d_min and a value d_max, the output of each filtering process K is the number of projected 1D diffraction vectors that are positioned within a box function, wherein the K value for the filter having the largest distance 'd*' between the boxes while maintaining a K value being at least X % of the maximum K value for all filters is selected as a measure F of the fit of the i'th new candidate lattice plane normal vector with the subset SSDV_n of 3D diffraction vectors, and wherein the vector pointing along the i'th new candidate lattice plane normal vector and having the length 1/'d*' is selected as a candidate direct-lattice vector whereby a set CDLV_n of candidate direct-lattice vectors is created, and wherein step (d_f_d) comprises:
- selecting three linear independent candidate direct-lattice vectors of the set CDLV_n based on their F values as the candidate unit cell CUC_n.
- X may be any percentage between 50% and 100% or 70% and 90% e.g. 80%.

In some embodiments, step (d_f_d) comprises:
- removing all candidate direct-lattice vectors from the set CDLV_n having a F value lower than Y % of the maximum F value of the set CDLV_n and selecting the three shortest linear independent candidate direct-lattice vectors remaining in the set CDLV_n as the candidate unit cell CUC_n.
- Y may be any percentage between 50% and 100% or 70% and 90% e.g. 80%.

In some embodiments, step (d_g) comprises determining the reciprocal lattice vectors for the candidate unit cel CUC_n and finding the number P of 3D diffraction vectors of the set DV being within a predetermined distance M from each reciprocal lattice point wherein said number P is a measure of the fit of the CUC_n with the set DV of 3D diffraction vectors.

In some embodiments, the subset ST of the set DV of 3D diffraction vectors originating from a single grain in the poly-crystal sample is identified by:
- determining the reciprocal lattice vectors for the primary candidate unit cell PCUC and selecting the 3D diffraction vectors of the set DV being within a predetermined distance M from each reciprocal lattice point.

M may be a number between 1e and 10e, between 3e and 7e e.g. 5e, where e is the experimental center-of-mass errors of the position of the reflections in sample space.

According to a second aspect the present invention relates to a method of indexing a plurality of diffraction spots, said method comprising the steps of:
- indexing the diffraction vectors corresponding to the plurality of diffraction spots using a method as disclosed in relation to the first aspect of the present invention; and using said indexed diffraction vectors to index said corresponding diffraction spots.

According to a third aspect the present invention relates to a method of determining the composition of a poly-crystalline sample comprising the steps of:
- illuminating a poly-crystalline sample with an X-ray source at a plurality of orientations and recording diffraction spots using at least one 2D or 3D X-ray detector for each of said plurality of orientations;
- transforming said recorded diffraction spots into a set DV of diffraction vectors;
- indexing said set DV of diffraction vectors using a method as disclosed in relation to the first aspect of the present invention;
- processing said indexed diffraction vectors to determine the composition of the poly-crystalline sample.

According to a fourth aspect, the present invention relates to a computer program product comprising program code means adapted to cause a data processing system to perform the steps of the method as disclosed in relation the any one of the embodiments of the first aspect of the present invention, when said program code means are executed on the data processing system.

In some embodiments, said computer program product comprises a non-transitory computer-readable medium having stored thereon the program code means.

According to a fifth aspect, the present invention relates to a data processing system configured to perform the method as disclosed in relation the any one of the embodiments of the first aspect of the present invention According to a sixth aspect, the present invention relates to an X-ray diffraction apparatus for analysing a poly-crystalline sample, comprising:
- an X-ray source for emitting an X-ray beam;
- a staging device for positioning the poly-crystalline sample in the beam path in a plurality of mutually different angular positions relative to the to the X-ray source;
- an X-ray detector for detecting diffracted X-ray beams leaving the poly-crystalline sample; and
- a processing unit operationally connected to said X-ray detector said processing unit being configured to determine a set DV of 3D diffraction vectors by processing data received from said X-ray detector obtained by illuminating the poly-crystalline sample at a plurality of orientations; and
- indexing said set DV of 3D diffraction vectors using a method as disclosed in relation the any one of the embodiments of the first aspect of the present invention.

The staging device may be movable, i.e. the staging device may rotate the sample. Alternatively/additionally the X-ray source and the X-ray detector may be movable, i.e. the X-ray source and the X-ray detector may be configured to orbit the sample.

According to a seventh aspect the present invention relates to a method of determining at least a first property of at least a first grain of a polycrystalline sample using at least one selected analysing method selected from the group of analysing methods consisting of: a reciprocal space mapping method, a defect studies method, and a method for finding the solution and the refinement of the at least the first grain, said method comprising the steps of:
- illuminating said poly-crystalline sample with an X-ray source at a plurality of orientations and recording diffraction spots using a 2D or 3D X-ray detector for each of said plurality of orientations;
- transforming said recorded diffraction spots into a set DV of diffraction vectors;
- indexing said set DV of diffraction vectors using a method according to any one of claims 1 to 10 to determine a subset of said set DV of diffraction vectors originating from said first grain; and
- analysing the diffraction vectors and/or their corresponding diffraction spots originating from said first grain using said selected analysing method to determine said at least first property of said first grain.

Examples of a reciprocal space mapping method may be found in [4] [5]. An example of a defect studies method may be found in [6]. Examples of methods for finding the solution and the refinement of a grain can be found in [7] [8].

Here and in the following, the term 'processing unit' is intended to comprise any circuit and/or device suitably adapted to perform the functions described herein. In particular, the above term comprises general purpose or proprietary programmable microprocessors, Digital Signal Processors (DSP), Application Specific Integrated Circuits (ASIC), Programmable Logic Arrays (PLA), Field Programmable Gate Arrays (FPGA), special-purpose electronic circuits, etc. or a combination thereof The different aspects of the present invention can be implemented in different ways as described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependant claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present invention will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the present invention may be practiced.

Figure 1:
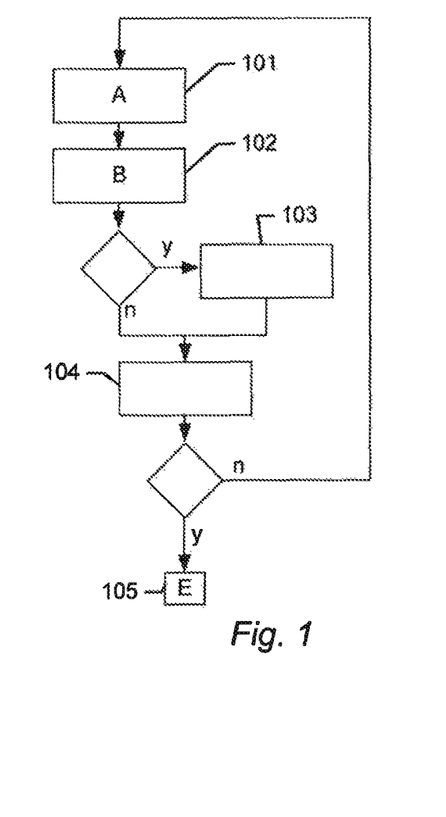
FIG. 1 shows a flowchart for a method of indexing a set DV of 3D diffraction vectors according to an embodiment of the present invention.

FIG. 1 shows a flowchart for a method of determining one or more unit cells of a poly-crystalline sample and indexing a set DV of 3D diffraction vectors according to an embodiment of the present invention. The set DV of 3D diffraction vectors is obtained by illuminating the poly-crystalline sample with an X-ray source at a plurality of orientations and recording diffraction spots using a 2D or 3D X-ray detector for each of the plurality of orientations. The set DV of 3D diffraction vectors is being indexed into a plurality of grains. The method starts in step 101 with obtaining a plurality of candidate first lattice plane normal vector and a plurality of candidate second lattice plane normal vectors for a particular grain. The candidate first and second lattice plane normal vectors are 3D vectors that may be generated by a pseudo random number generator (PRNG). Next, the plurality of candidate first lattice plane normal vectors and the plurality of candidate second lattice plane normal vectors are used to select a plurality of subsets SSDV_n (n=1 to N1) of the set DV of 3D diffraction vectors. These subsets SSDV_n are processed to determine a primary candidate unit cell PCUC defined by three lattice vectors. The primary candidate unit cell PCUC is validated by evaluating the fit of the PCUC with the full set DV of 3D diffraction vectors. Next, the method continues to step B 102 where it is determined if the fit of the primary candidate unit cell PCUC with the full set DV of 3D diffraction vectors is above a first threshold. If the fit is above the first threshold the method continues to step 103 where the primary candidate unit cell PCUC is used to identify a subset ST of the set DV of 3D diffraction vectors originating from a single grain. The subset ST is then indexed and removed from the set DV of 3D diffraction vectors and the method continues to step 104. Alternatively, if the fit is found to be below the first threshold the method skips step 103 and continues directly from step 102 to step 104. In step 104 the method determines if a first predetermined criteria has been reached. Examples of a predetermined criteria are: that all indexable grains in the poly-crystal sample have been indexed, that a predetermined number of grains have been indexed, that a predetermined percentage of the diffraction vectors has been indexed, that the remaining diffraction vectors is below a predetermined number, or that step (A) and (B) have been repeated a predetermined number of times without identifying any new grains. If the predetermined criteria has not yet been reached the method returns to step A to look for a new primary candidate unit cell PCUC. Alternatively, if the predetermined criteria have been reached the method terminates in step 105.

Figure 2:
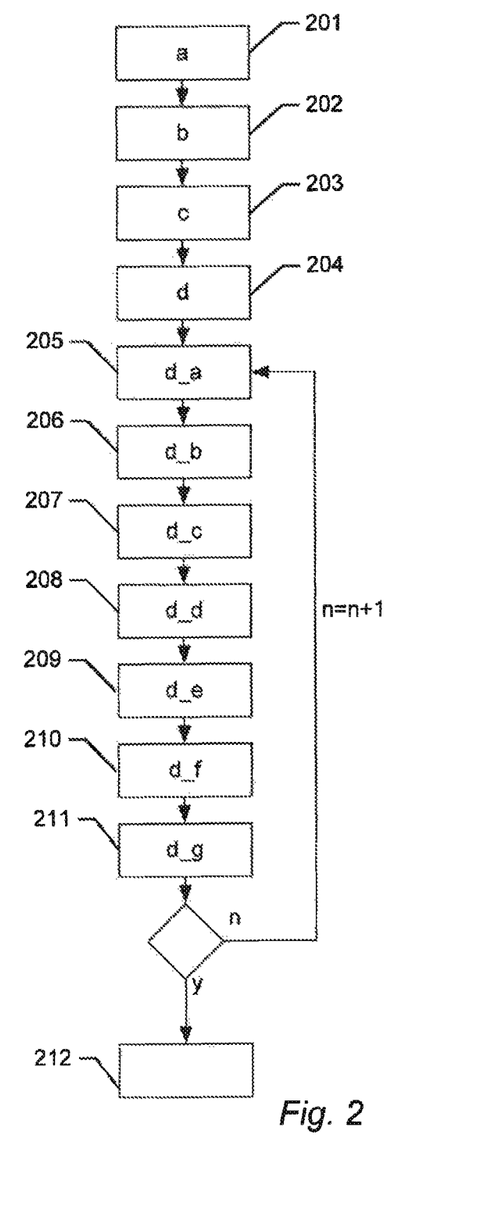
FIG. 2 show a flowchart for a first part of a method according to an embodiment of the present invention.

FIG. 2 shows a flowchart for a first part of a method according to an embodiment of the present invention. Specifically FIG. 2 shows how step A in the method disclosed in relation to FIG. 1 may be carried out. Firstly, in step 201 a set L1 of candidate first lattice plane normal vectors are selected. The set L1 may be selected using a PRNG. Next, in step 202 the fit of each candidate first lattice plane normal vector of the set L1 with the set DV of 3D diffraction vectors is evaluated. Then, in step 203 a subset SL1 of the set L1 comprising the N1 candidate first lattice plane normal vectors having the best fit with the set DV of 3D diffraction vectors is selected. Next, in step 204, for each individual candidate first lattice plane normal vector of the subset SL1 steps 205-211 are performed.

First, in step 205 the n'th (starting with n=1) candidate first lattice plane normal vector of the subset SL1 is used to select a subset SDV_n of the set DV of 3D diffraction vectors. Next, in step 206 a set L2_*n* of candidate second lattice plane normal vectors is selected. The set L2_*n* may be selected using a PRNG. Then, in step 207 the fit of each candidate second lattice plane normal vector of the set L2_*n* with the subset SDV_n of 3D diffraction vectors is evaluated. Next, in step 208 a subset SL2_*n* of the set L2_*n* is selected comprising the N2 candidate second lattice plane normal vectors having the best fit with the subset SDV_n of 3D diffraction vectors. Then, in step 209 the subset SL2_*n* of candidate second lattice plane normal vectors is used to select a subset SSDV_n of the subset SDV_n of 3D diffraction vectors. The subset SSDV_n of 3D diffraction vectors is then in step 210 processed to determine a candidate unit cell CUC_n defined by three lattice vectors, and finally in step 211 the fit of the candidate unit cell CUC_n with the set full set DV of 3D diffraction vectors is evaluated. The method then returns to step 205 if n is below N1 and increases n by 1. Alternatively, if n is equal to N1 (meaning that steps 205-211 have been performed for each candidate first lattice plane normal vector of the subset SL1) the method continues to step 212 where the candidate unit cell of the N1 candidate unit cells CUC_n (n=1 to N1) having the best fit with the full set DV of 3D diffraction vectors is selected as the primary candidate unit cell PCUC.

Figure 3:
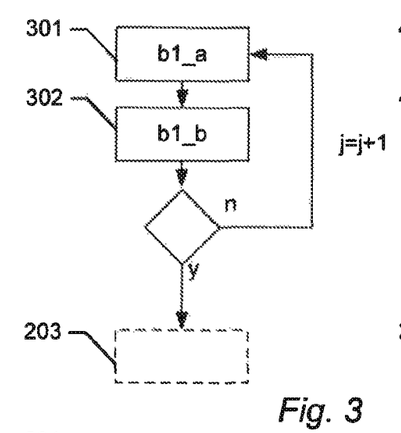
FIG. 3 show a flowchart for a second part of a method according to an embodiment of the present invention.

FIG. 3 shows a flowchart for a second part of a method according to an embodiment of the present invention. Specifically FIG. 3 shows an example of how step 202 in the method disclosed in relation to FIG. 2 may be carried out.

For each candidate first lattice plane normal vector of the set L1 steps 301 and 302 are performed. First, in step 301 the set DV of 3D diffraction vectors is projected onto the j'th (starting with j=1) candidate first lattice plane normal vector resulting in a set DV1D_j of projected 1D diffraction vectors. Next, in step 302 the set DV1D_j of projected 1D diffraction vectors is filtered with a plurality of filters comprising a regular array of box functions, the width of the boxes being the same for all filter but the distance 'd' between the boxes is increased from a value d_min to a value d_max (in increasingly larger steps), the output of each filtering process K is the normalised number of projected 1D diffraction vectors that are positioned within a box function, wherein the highest K value is used as a measure of the fit of the j'th candidate first lattice plane normal vector with the set DV of 3D diffraction vectors. The method then returns to step 301 if j is below N1 (N1 being equal to the number of candidate first lattice plane normal vectors in the set L1) and increases n by 1. Alternatively, if j is equal to N1 (meaning that steps 201 and 202 have been performed for each candidate first lattice plane normal vector of the set L1) the method continues to step 203 in FIG. 2.

Figure 7A:
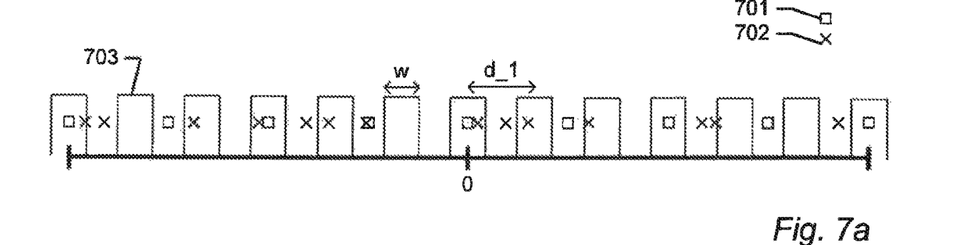
FIG. 7a-c illustrates schematically a filtering process according to an embodiment of the present invention.
Figure 7B:
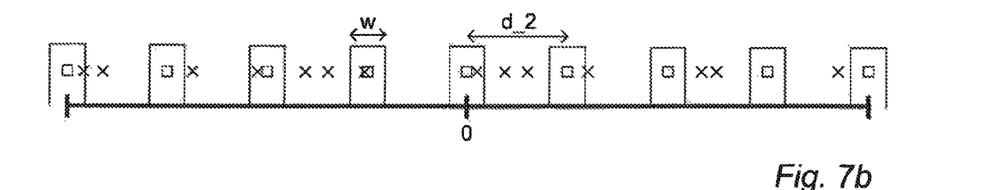

FIGS. 7*a-b* illustrates schematically the filtering process. In this simplified example only 23 diffraction vectors originating from a first grain and a second grain are present. However, normally the number of diffraction vectors and grains will be much larger. The terminal point for the projected 1D diffraction vectors originating from the first grain are shown as boxes 701 and the terminal point of the projected 1D diffractions vectors originating from the second grain are shown as crosses 702. Thus, there are 9 projected 1D diffraction vectors originating from the first grain and 14 originating from the second grain. The 23 3D diffraction vectors are in Figs. a-b projected onto a candidate lattice plane normal vector that is identical to one of the three true lattice plane normal vectors for the first grain but not identical to any one of the three true lattice plane normal vectors for the second grain. Consequently, the projected 1D diffraction vectors originating from the first grain are arranged with a regular spacing, and the projected 1D diffraction vectors originating from the second grain are arranged with an irregular spacing.

FIG. 7a illustrates a first filtering process. Shown is a regular array of box functions 703 having a width w and being arranged with a distance 'd_1'. The distance 'd_1' is measured between the centre of two neighbouring box functions. For this filtering process the distance 'd_1' between the boxes does not match the regular spacing between 1D diffraction vectors originating from the first grain. The number of diffraction vectors arranged within a box function is in this example 12, to get output K of the filtering process this number is 'normalized' by subtracting the expected number of diffraction vectors that by chance will be arranged within a box function. Using equation (1) this number is found to be 0.53*23=12,19. Thus the output K of the filtering process is −0.19.

FIG. 7b illustrates a second filtering process. Shown is a regular array of box functions 703 having a width w and being arranged with a distance 'd_2'. The width w is the same for both filtering process but 'd_2' is larer than 'd_1'. For this filtering process the distance 'd_2' between the boxes matches the regular spacing between 1D diffraction vectors originating from the first grain. The number of diffraction vectors arranged within a box function is in this example 13, to get the output K of the filtering process this number is 'normalized' by subtracting the expected number of diffraction vectors that by chance will be arranged within a box function. Again using equation (1) this number is found to be 0.35*23=8. Thus the output K of the filtering process is 5.

Figure 7C:
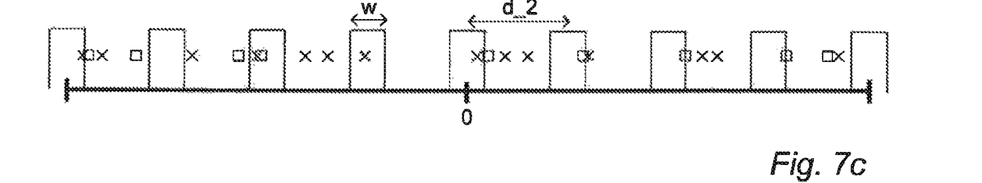

FIG. 7c shows the 23 3D diffraction vectors projected onto a candidate lattice plane normal vector that is non-identical to any one of the three true lattice plane normal vectors for both the first and the second grain. Consequently, the projected 1D diffraction vectors originating from the both the first and the second grain are arranged with an irregular spacing.

As an alternative to the filtering process disclosed in relation to FIG. 7 a method based on frequency analysis may be used to evaluate the fit of each candidate lattice plane normal vector. This may be done by sampling the project 1D diffraction vectors to create a sampled signal, and determining the amplitude spectrum for the sampled signal. By studying the amplitude spectrum in the frequency range between 1/d_max to 1/d_min the fit of the candidate lattice plane normal vectors with the set DV of 3D diffraction vectors may be determined e.g. by examining the peak amplitude within that frequency range.

Figure 8:
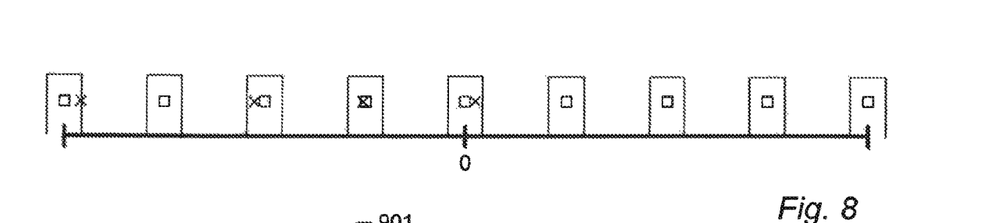
FIG. 8 illustrates schematically a filtering process according to an embodiment of the present invention.

FIG. 8 shows the subset of the projected 23 diffraction vectors shown in FIG. 7a-b that are positioned within a box function for the filter having the highest K value (the filter shown in FIG. 7b).

Figure 4:
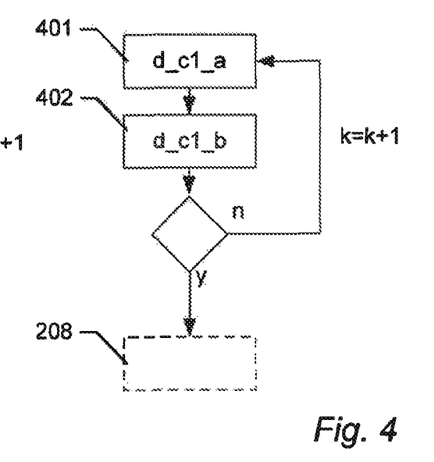
FIG. 4 show a flowchart for a third part of a method according to an embodiment of the present invention.

FIG. 4 shows a flowchart for a third part of a method according to an embodiment of the present invention. Specifically FIG. 4 shows an example of how step 207 in the method disclosed in relation to FIG. 2 may be carried out. For each candidate second lattice plane normal vector of the set L2_n steps 401 and 402 are performed. First, in step 401 the subset SDV_n of 3D diffraction vectors is projected onto the k candidate second lattice plane normal vector resulting in a set SDV_n1D_n of projected 1D diffraction vectors. Then, the set SDV_n1D_k of projected 1D diffraction vectors is filtered with a plurality of filters comprising a regular array of box functions, the width of the boxes being the same for all filter but the distance 'd' between the boxes is increased from a value d_min to a value d_max (in increasingly larger steps), the output of each filtering process K is the normalized number of projected 1D diffraction vectors that are positioned within a box function, wherein the highest K value is used as a measure of the fit of the k'th candidate second lattice plane normal vector with the set SDV_n of 3D diffraction vectors. The filtering process may be performed using the same principles disclosed in relation to FIG. 7.

The method then returns to step 401 if k is below N2 (N2 being equal to the number of candidate second lattice plane normal vectors in the set L2_n) and increases k by 1. Alternatively, if k is equal to N2 (meaning that steps 301 and 302 have been performed for each candidate second lattice plane normal vector of the set L2_n) the method continues to step 208 in FIG. 2.

Figure 5:
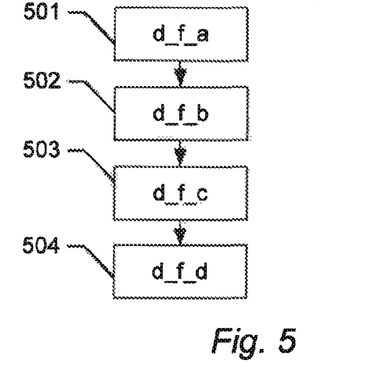
FIG. 5 show a flowchart for a fourth part of a method according to an embodiment of the present invention.

FIG. 5 shows a flowchart for a fourth part of a method according to an embodiment of the present invention. Specifically FIG. 5 shows an example of how step 210 in the method disclosed in relation to FIG. 2 may be carried out. The method starts in step 501 with selecting a subset SSSDV_n of the subset SSDV_n of 3D diffraction vectors. The subset SSSDV_n may comprise the 50 shortest diffraction vectors of the subset SSDV_n of 3D diffraction vectors. The method then continues to step 502 where the normal vector for all planes spanned by three diffraction vectors of the subset SSSDV_n of 3D diffraction vectors (ignoring sets of three diffraction vectors having a cross product close to zero) are determined. Since each normal vector is a candidate lattice plane normal vector this result in a set NL_n of new candidate lattice plane normal vectors. Next, in step 503, the fit of each new candidate lattice plane normal vector of the set NL_n with the subset SSDV_n of 3D diffraction vectors is evaluated, and finally in step 504 a candidate unit cell CUC_n is determined. The method then continues to step 212 in FIG. 2.

Figure 6:
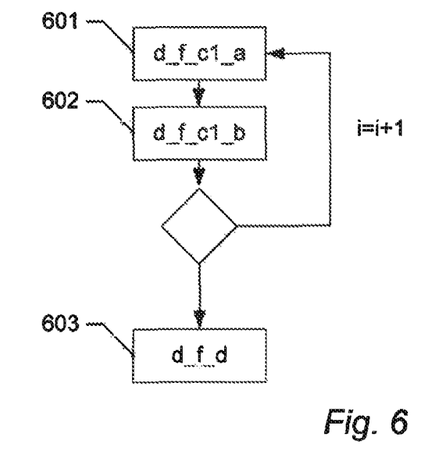
FIG. 6 show a flowchart for a fifth part of a method according to an embodiment of the present invention.

FIG. 6 shows a flowchart for a fifth part of a method according to an embodiment of the present invention. Specifically FIG. 6 shows an example of how steps 503 and 504 in the method disclosed in relation to FIG. 5 may be carried out.

For each new candidate lattice plane normal vector of the set NL_n steps 601 and 602 are performed. First, in step 601 the subset SSDV_n of 3D diffraction vectors is projected onto the i'th (starting with i=1) new candidate lattice plane normal vector resulting in a set SSDV_n_1D_i of 1D diffraction vectors. Next in step 602, the set SSDV_n_1D_i of projected 1D diffraction vectors is filtered with a plurality of filters comprising a regular array of box functions, the width of the boxes being the same for all filter but the distance 'd' between the boxes is increased between a value d_min and a value d_max, the output of each filtering process K is the number of projected 1D diffraction vectors that are positioned within a box function, wherein the K value for the filter having the largest distance 'd*' between the boxes while maintaining a K value being at least X % of the maximum K value for all filters is selected as a measure F of the fit of the i'th new candidate lattice plane normal vector with the subset SSDV_n of 3D diffraction vectors, and wherein the vector pointing along the i'th new candidate lattice plane normal vector and having the length 1/'d*' is selected as a candidate direct-lattice vector. The method then returns to step 601 if i is below N4 (N4 being equal to the number of new candidate lattice plane normal vector of the set NL_n) and increases i by 1. Alternatively, if i is equal to N4 (meaning that steps 601 and 602 have been performed for each new candidate lattice plane normal vector of the set NL_n) the method continues to step 603. This result in a set CDLV_n of candidate direct-lattice vectors comprising N4 candidate direct-lattice vectors. In the 603, three linear independent candidate direct-lattice vectors of the set CDLV_n is selected as the candidate unit cell CUC_n based on their respective F values.

Figure 9:
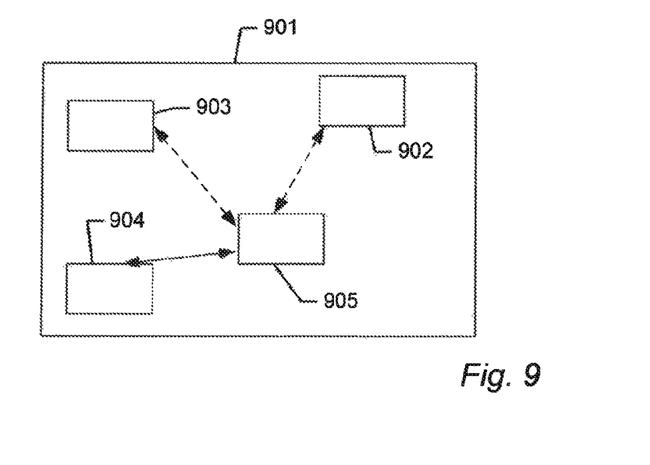
FIG. 9 shows a schematic drawing of an X-ray diffraction apparatus according to an embodiment of the present invention.

FIG. 9 shows a schematic drawing of an X-ray diffraction apparatus 901 for analysing a poly-crystalline sample according to an embodiment of the present invention. The X-ray diffraction apparatus comprises:

an X-ray source 902 for emitting an X-ray beam; a staging device 903 for positioning the poly-crystalline sample in the beam path in a plurality of mutually different angular positions in relation to the X-ray source 902; an X-ray detector 904 for detecting at least diffracted X-ray beams leaving the poly-crystalline sample; and a processing unit 905 operationally connected to at least the X-ray detector 904. The processing unit 905 is preferably also operationally connected to the X-ray source 902 and the staging device 903 enabling the processing unit to control them. The processing unit 905 is configured to determine a set DV of 3D diffraction vectors by processing data received from said X-ray detector obtained by illuminating the poly-crystalline sample at a plurality of orientations; and indexing the set DV of 3D diffraction vectors using a method as disclosed in relation the any one of the embodiments of the first aspect of the present invention and or the embodiments disclosed in relation to any one of FIGS. 1 to 8.

FIGS. 10*a*-*b* show schematically how diffraction spots may be recorded and transformed into diffraction vectors. The set of diffraction vectors can be determined in a number of ways. The most commonly used is the "rotation method" known from single-crystal crystallography [9] in which case the sample to detector distance 1013 is sufficiently large that all grains can be considered to be located at the origin of the sample (i.e. a far-field configuration). In such a setup a monochromatic x-ray beam 1001 is illuminating the sample 1005 through an aperture 1002 and a beam stop 1004 and a detector 1007 is provided behind the sample 1005. The sample 1005 is mounted on a rotation stage with one or more rotational axes 1003. In one embodiment, the sample is rotated around a single axis 1003 perpendicular to the incoming beam as illustrated in FIG. 10*a*. As an option, x, y and z translations may be added, as well as additional rotations. Any part of the illuminated structure which fulfills the Bragg condition 1012 (e.g. a lattice plane) will generate a diffracted beam 1006. Images are acquired from multiple rotational positions of the sample to ensure multiple diffraction spots 1008 from all illuminated grains. In this monochromatic far-field configuration the diffraction vectors 1011 are derived from knowledge of the incoming beam direction 1009 and the directional vectors 1010 from the sample origin to the measure diffraction spots on the detector(s) 1007 (See FIG. 10*b*). Other examples of experimental methods for measuring diffractions vectors include monochromatic near-field configurations such as those described in [10], and [11], as well as polychromatic configurations (see e.g. [12] and [13]).

Although some embodiments have been described and shown in detail, the present invention is not restricted to them, but may also be embodied in other ways within the scope of the subject matter defined in the following claims. In particular, it is to be understood that other embodiments may be utilized and structural and functional modifications may be made without departing from the scope of the present invention.

In system claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.'

REFERENCES

[1] Srensen et al. 2012b Z. Kristall. 227, 63-78
[2] Gruber, B. (1973). Acta Cryst. A29, 433-440
[3] Grosse-Kunstleve, R. W., Sauter, N. K. & Adams, P. D. (2004). Acta Cryst. A60, 1-6.
[4] Jakobsen, B., Poulsen, H. F., Lienert, U. & Pantleon, W. (2007). Acta Mater. 55, 3421-3430
[5] Wejdemann, C., Poulsen, H. F., Lienert, U. & Pantleon, W. (2013). JOM. 65, 35-43
[6] Ungar, T., Ribarik, G., Balogh, L., Salem, A. A., Semiatin, S. L. & Vaughan, G. B. M. (2010). Scripta Mater. 63, 69-72
[7] Schmidt, S. (2014). J. Appl. Cryst. 47, 276-284
[8] Srensen, H. O., Schmidt, S., Wright, J. P., Vaughan, G. B. M., Techert, S., Garman, E. F., Oddershede, J., Davaasambu, J., Paithankar, K. S., Gundlach, C., & Poulsen H. F. (2012b). Z
[9] C. Giacovazzo, H. L. Monaco, D. Viterbo, F. Scordari, G. Gilli, G. Zanotti, M. Catti: Fundamentals of Crystallography, IUCr Texts on Crystallography, No. 2 (Oxford University Press, Oxford 1992)
[10] E. M. Lauridsen, S. Schmidt, R. M. Suter, H. F. Poulsen (2001), Tracking: A method for structural characterization of grains in powders or polycrystals, J. Appl. Cryst., Vol. 34, 744-750
[11] Ludwig, W., P. Reischig, A. King, M. Herbig, E. M. Lauridsen, G. Johnson, T. J. Marrow, J. Y. Buffiere; Three-dimensional grain mapping by x-ray diffraction contrast tomography and the use of Friedel pairs in diffraction data analysis, Review of Scientific Intruments, 2009, 80(3):033905
[12] Larson, B. C., Yang, W., Ice, G. E., Budai, J. D. & Tischler, J. Z. (2002). Nature, 415, 887-890.
[13] A. King, P. Reischig, J. Adrien, W. Ludwig, First laboratory X-ray diffraction contrast tomography for grain mapping of polycrystals, J. Appl. Cryst. (2013). 46, 1734-1740

The invention claimed is:

1. A method of determining one or more unit cells of a poly-crystalline sample and indexing a set DV of 3D diffraction vectors obtained by illuminating said poly-crystalline sample with an X-ray source at one or more orientations and recording diffraction spots using a at least one 2D or 3D X-ray detector for each of said one or more orientations, said set DV of 3D diffraction vectors being indexed into a plurality of grains, said method comprising the steps of:

(A) obtaining a plurality of candidate first lattice plane normal vectors and a plurality of candidate second lattice plane normal vectors for a particular unknown grain; using said plurality of candidate first lattice plane normal vectors and said plurality of candidate second lattice plane normal vectors to select a plurality of subsets SSDV_n of the set DV of 3D diffraction vectors and processing said plurality of subsets SSDV_n of 3D diffraction vectors to determine a primary candidate unit cell PCUC defined by three lattice vectors; wherein the correspondence of the primary candidate unit cell PCUC is validated by evaluating the fit of the PCUC with the full set DV of 3D diffraction vectors; and (B) determining if the fit of primary candidate unit cell PCUC with the full set DV of 3D diffraction vectors is above a first threshold;

wherein if the fit of the primary candidate unit cell PCUC is above said first threshold the primary candidate unit cell PCUC is used to identify a subset ST of the set DV of 3D diffraction vectors originating from a single grain in the poly-crystalline sample, said subset ST is indexed wherein the method returns to step (A) unless a predetermined criteria has been reached;

wherein step (A) further comprises the steps of
(a) selecting a set L1 of candidate first lattice plane normal vectors;
(b) evaluating the fit of each candidate first lattice plane normal vector of the set L1 with the set DV of 3D diffraction vectors;
(c) selecting a subset SL1 of the set L1 comprising the N1 candidate first lattice plane normal vectors having the best fit with the set DV of 3D diffraction vectors;
(d) performing steps (d_a) to (d_g) for each candidate first lattice plane normal vector n of the subset SL1:
(d_a) using said candidate first lattice plane normal vector n to select a subset SDV_n of the set DV of 3D diffraction vectors;
(d_b) selecting a set L2_$n$ of candidate second lattice plane normal vectors;
(d_c) evaluating the fit of each candidate second lattice plane normal vector of the set L2_$n$ with the subset SDV_n of 3D diffraction vectors;
(d_d) selecting a subset SL2_$n$ of the set L2_$n$ comprising the N2 candidate second lattice plane normal vectors having the best fit with the subset SDV_n of 3D diffraction vectors;
(d_e) using said subset SL2_$n$ of candidate second lattice plane normal vectors to select a subset SSDV_n of the subset SDV_n of 3D diffraction vectors;
(d_f) processing said subset SSDV_n of 3D diffraction vectors to determine a candidate unit cell CUC_n defined by three lattice vectors;
(d_g) evaluating the fit of the candidate unit cell CUC_n with the set DV of 3D diffraction vectors;
wherein the candidate unit cell of the N1 candidate unit cells CUC_n (n=1 to N1) having the best fit with the full set DV of 3D diffraction vectors is selected as the primary candidate unit cell PCUC.

2. A method according to claim 1, wherein step (b) comprises the steps of:
(b1) performing steps (b1_a) and (b1_b) for each j candidate first lattice plane normal vector of the set L1:
(b1_a) projecting the set DV of 3D diffraction vectors onto said j candidate first lattice plane normal vector resulting in a set DV1D_j of projected 1D diffraction vectors;
(b1_b) filtering the set DV1D_j of projected 1D diffraction vectors with a plurality of filters comprising a regular array of box functions, the width of the boxes being the same for all filter but the distance 'd' between the boxes is increased from a value d_min to a value d_max, the output of each filtering process K is the normalised number of projected 1D diffraction vectors that are positioned within a box function, wherein the highest K value is used as a measure of the fit of the n'th candidate first lattice plane normal vector with the set DV of 3D diffraction vectors; and wherein step (c) comprises selecting the N1 candidate first lattice plane normal vectors having the highest K value.

3. A method according to claim 1, wherein step (c) further comprises for each n candidate first lattice plane normal vector of the subset SL1, optimizing the n candidate first lattice plane normal vector by performing a local grid search resulting in an subset SL1* of optimized candidate first lattice plane normal vectors, wherein the optimized subset SL1* is used in step (d).

4. A method according to claim 1, wherein step (d_c) comprises the steps of:
(d_c1) performing steps (d_c1_a) and (d_c1_b) for each k candidate second lattice plane normal vector of the set L2_$n$:
(d_c1_a) projecting the subset SDV_n of 3D diffraction vectors onto said k candidate second lattice plane normal vector resulting in a set SDV_$n$1D_n of projected 1D diffraction vectors;
(d_c1_b) filtering the set SDV_$n$1D_k of projected 1D diffraction vectors with a plurality of filters comprising a regular array of box functions, the width of the boxes being the same for all filter but the distance 'd' between the boxes is increased from a value d_min to a value d_max, the output of each filtering process K is the normalized number of projected 1D diffraction vectors that are positioned within a box function, wherein the highest K value is used as a measure of the fit of the k'th candidate second lattice plane normal vector with the set SDV_n of 3D diffraction vectors; and
wherein step (d_d) comprises selecting the N3 candidate second lattice plane normal vectors having the highest K value.

5. A method according to claim 1, wherein step (d_d) further comprises for each k candidate second lattice plane normal vector of the subset SL2_$n$, optimizing the k candidate second lattice plane normal vector by performing a local grid search resulting in an subset SL2_$n$* of optimized candidate second lattice plane normal vectors, wherein the optimized subset SL2_$n$* is used in step (d_e).

6. A method according to claim 5, wherein the candidate second lattice plane normal vector CL2_$n$ of the subset SL2_$n$* having the best fit with the subset SDV_n of 3D diffraction vectors is used to select the subset SSDV_n of the subset SDV_n of 3D diffraction vectors.

7. A method according to claim 1, wherein step (d_e) comprises selecting the 3D diffraction vectors of the subset SDV_n that when they are projected onto CL2_$n$ are positioned within a box function for the filter having the highest K value.

8. A method according to claim 1, wherein step (d_f) comprises the steps of:
(d_f_a) selecting a subset SSSDV_n of the subset SSDV_n of 3D diffraction vectors;
(d_f_b) determining the normal vector for all planes spanned by three diffraction vectors of the subset SSSDV_n of 3D diffraction vectors (ignoring sets of three diffraction vectors having a cross product close to zero) each normal vector being a candidate lattice plane normal vector thereby resulting in a set NL_n of new candidate lattice plane normal vectors;

(d_f_c) evaluating the fit of each new candidate lattice plane normal vector of the set NL_n with the subset SSDV_n of 3D diffraction vectors; and (d_f_d) determining a candidate unit cell CUC_n.

9. A method according to claim 8, wherein step (d_f_c) comprises:

(d_f_c1) performing steps (d_f_c1_a) and (d_f_c1_b) for each i new candidate lattice plane normal vector of the set NL_n:

(d_f_c1_a) projecting the subset SSDV_n of 3D diffraction vectors onto said i new candidate lattice plane normal vector resulting in a set SSDV_n_1D_i of 1D diffraction vectors;

(d_f_c1_b) filtering the set SSDV_n_1D_i of projected 1D diffraction vectors with a plurality of filters comprising a regular array of box functions, the width of the boxes being the same for all filter but the distance 'd' between the boxes is increased between a value d_min and a value d_max, the output of each filtering process K is the number of projected 1D diffraction vectors that are positioned within a box function, wherein the K value for the filter having the largest distance 'd*' between the boxes while maintaining a K value being at least X % of the maximum K value for all filters is selected as a measure F of the fit of the i'th new candidate lattice plane normal vector with the subset SSDV_n of 3D diffraction vectors, and wherein the vector pointing along the i'th new candidate lattice plane normal vector and having the length 1/'d*' is selected as a candidate direct-lattice vector whereby a set CDLV_n of candidate direct-lattice vectors is created, and wherein step (d_f_d) comprises:

selecting three linear independent candidate direct-lattice vectors of the set CDLV_n based on their F values as the candidate unit cell CUC_n.

10. A method of indexing a plurality of diffraction spots, said method comprising the steps of:

indexing the diffraction vectors corresponding to the plurality of diffraction spots using a method according to claim 1; and using said indexed diffraction vectors to index said corresponding diffraction spots.

11. A method of determining the composition of a poly-crystalline sample comprising the steps of:

illuminating a poly-crystalline sample with an X-ray source at a plurality of orientations and recording diffraction spots using a 2D or 3D X-ray detector for each of said plurality of orientations;

transforming said recorded diffraction spots into a set DV of diffraction vectors;

indexing said set DV of diffraction vectors using a method according to claim 1; and processing said indexed diffraction vectors to determine the composition of the poly-crystal sample.

12. A computer program product comprising program code means adapted to cause a data processing system to perform the steps of the method according to claim 1, when said program code means are executed on the data processing system.

13. A computer program product according to claim 12, wherein said computer program product comprises a non-transitory computer-readable medium having stored thereon the program code means.

14. An X-ray diffraction apparatus for analysing a poly-crystalline sample, comprising:

an X-ray source for emitting an X-ray beam;

a staging device for positioning the poly-crystalline sample in the beam path in a plurality of mutually different angular positions relative to the to the X-ray source;

an X-ray detector for detecting diffracted X-ray beams leaving the poly-crystalline sample; and a processing unit operationally connected to said X-ray detector said processing unit being configured to determine a set DV of 3D diffraction vectors by processing data received from said X-ray detector obtained by illuminating the poly-crystalline sample at a plurality of orientations; and indexing said set DV of 3D diffraction vectors using a method according to claim 1.

* * * * *